(12) United States Patent
Yamada

(10) Patent No.: US 11,710,567 B2
(45) Date of Patent: Jul. 25, 2023

(54) INFORMATION PROCESSING APPARATUS, INFORMATION PROCESSING METHOD, AND PROGRAM

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 555 days.

(21) Appl. No.: 16/660,766

(22) Filed: Oct. 22, 2019

(65) Prior Publication Data
US 2020/0135328 A1 Apr. 30, 2020

(30) Foreign Application Priority Data
Oct. 29, 2018 (JP) ................................. 2018-202948

(51) Int. Cl.
*G16H 50/20* (2018.01)
*G16H 15/00* (2018.01)
(Continued)

(52) U.S. Cl.
CPC ......... *G16H 50/20* (2018.01); *G06F 18/2178* (2023.01); *G06F 18/41* (2023.01);
(Continued)

(58) Field of Classification Search
CPC .. G06Q 50/20–26; G16H 30/20; G16H 15/00; G16H 20/00; G16H 20/10;
(Continued)

(56) References Cited

U.S. PATENT DOCUMENTS 6,084,981 A * 7/2000 Horiba .................... G06T 5/002
382/157
10,803,398 B2 10/2020 Yokono et al.
(Continued)

FOREIGN PATENT DOCUMENTS

JP H0554014 3/1993
JP H07-65168 3/1995
(Continued)

OTHER PUBLICATIONS

S.B. Kotsiantis, "Supervised Machine Learning: A Review of Classification Techniques", Jul. 16, 2007, Informatica 31 (2007) 249-268, all pages. (Year: 2007).*
(Continued)

*Primary Examiner* — Jason S Tiedeman
*Assistant Examiner* — Jessica Marie Webb
(74) *Attorney, Agent, or Firm* — JCIPRNET

(57) ABSTRACT

Provided are an information processing apparatus, an information processing method, and a program capable of accumulating appropriate relearning data. An information processing apparatus includes an input unit that inputs input data to a learned model acquired in advance through machine learning using learning data, an acquisition unit that acquires output data output from the learned model through the input using the input unit, a reception unit that receives correction performed by a user for the output data acquired by the acquisition unit, and a storage controller that performs control for storing, as relearning data of the learned model, the input data and the output data that reflects the correction received by the reception unit in a storage unit in a case where a value indicating a correction amount acquired by performing the correction for the output data is equal to or greater than a threshold value.

11 Claims, 7 Drawing Sheets

(51) Int. Cl.
*G16H 30/20* (2018.01)
*G06N 20/00* (2019.01)
*G06T 7/11* (2017.01)
*G16H 20/10* (2018.01)
*G06V 10/778* (2022.01)
*G06F 18/40* (2023.01)
*G06F 18/21* (2023.01)

(52) U.S. Cl.
CPC ............... *G06N 20/00* (2019.01); *G06T 7/11* (2017.01); *G06V 10/7784* (2022.01); *G06V 10/7788* (2022.01); *G16H 15/00* (2018.01); *G16H 20/10* (2018.01); *G16H 30/20* (2018.01); *G06V 2201/03* (2022.01)

(58) Field of Classification Search
CPC ........ G16H 20/20; G06K 9/00; G06K 9/6254; G06K 9/6263; G06V 2201/00; G06V 2201/03; G06V 2201/031; G06V 2201/032; G06V 2201/033; G06V 2201/034; G06N 20/00; G06N 20/10; G06N 20/20
See application file for complete search history.

(56) References Cited

U.S. PATENT DOCUMENTS

| | | | |
|---|---|---|---|
| 11,151,896 B2 * | 10/2021 | Letzt | G16H 40/67 |
| 2004/0122706 A1 * | 6/2004 | Walker | G16H 50/20 705/2 |
| 2008/0008369 A1 * | 1/2008 | Koptenko | G06T 7/12 382/199 |
| 2008/0243886 A1 * | 10/2008 | Oosawa | G16H 30/40 |
| 2011/0317888 A1 * | 12/2011 | Simon | G06V 10/755 382/128 |
| 2013/0163836 A1 * | 6/2013 | Pau | G06T 17/00 382/128 |
| 2016/0196389 A1 * | 7/2016 | Moturu | G16H 50/20 705/2 |
| 2016/0203599 A1 * | 7/2016 | Gillies | A61B 6/5211 382/132 |
| 2016/0300026 A1 * | 10/2016 | Bogoni | A61B 5/1075 |
| 2018/0032841 A1 * | 2/2018 | Kluckner | G16H 40/67 |
| 2018/0122509 A1 * | 5/2018 | Christiansson | G16H 10/60 |
| 2018/0137244 A1 * | 5/2018 | Sorenson | G16H 50/20 |
| 2018/0144466 A1 * | 5/2018 | Hsieh | G06T 7/0012 |
| 2018/0260951 A1 * | 9/2018 | Yang | G06K 9/6267 |
| 2018/0366225 A1 * | 12/2018 | Mansi | H04L 67/12 |
| 2019/0104940 A1 * | 4/2019 | Zhou | A61B 5/0073 |
| 2019/0117090 A1 * | 4/2019 | Ishii | G16H 50/20 |
| 2019/0147334 A1 * | 5/2019 | Lisowska | G06N 3/088 706/25 |
| 2019/0213285 A1 * | 7/2019 | Baggeroer | G06N 7/005 |
| 2019/0311805 A1 * | 10/2019 | Linguraru | G06K 9/6256 |
| 2020/0074224 A1 * | 3/2020 | Hayashi | G06F 3/14 |
| 2020/0118265 A1 * | 4/2020 | Igarashi | G16H 30/20 |
| 2020/0218943 A1 * | 7/2020 | Osake | G06K 9/6262 |
| 2020/0372635 A1 * | 11/2020 | Veidman | G06T 7/0012 |
| 2021/0073096 A1 * | 3/2021 | Kato | B25J 19/06 |
| 2021/0272288 A1 * | 9/2021 | Takahashi | G06N 20/00 |

FOREIGN PATENT DOCUMENTS

| | | | |
|---|---|---|---|
| JP | H0997245 | 4/1997 | |
| JP | 2013-041323 | 2/2013 | |
| JP | 2015087903 | 5/2015 | |
| JP | 2016161823 | 9/2016 | |
| RU | 2529381 C2 * | 9/2014 | ............ G16H 70/20 |
| WO | WO-2019051359 A1 * | 3/2019 | ........... G06K 9/6259 |

OTHER PUBLICATIONS

L. C. Rabelo, A. Jones and Y. Yih, "Development of a real-time learning scheduler using reinforcement learning concepts," Proceedings of 1994 9th IEEE International Symposium on Intelligent Control, Columbus, OH, USA, 1994, pp. 291-296, doi: 10.1109/ISIC.1994.367802. (Year: 1994).*

MRbOneS et al., "Thresholds in backpropagation", 2015, Stack Exchange, Inc., forum, all pages, URL: https://stackoverflow.com/questions/31227533/thresholds-in-backpropagation. (Year: 2015).*

Sterling, Mary J. "Rules for Operations on Inequalities". Jul. 27, 2018. Dummies, all pages. https://www.dummies.com/article/business-careers-money/business/accounting/calculation-analysis/rules-operations-inequalities-254754 (Year: 2018).*

"Office Action of Japan Counterpart Application", dated Jan. 25, 2022, with English translation thereof, pp. 1-8.

* cited by examiner

INFORMATION PROCESSING APPARATUS, INFORMATION PROCESSING METHOD, AND PROGRAM

CROSS-REFERENCE TO RELATED APPLICATION

This application claims priority under 35 USC 119 from Japanese Patent Application No. 2018-202948 filed on Oct. 29, 2018, the disclosure of which is incorporated by reference herein in its entirety.

BACKGROUND OF THE INVENTION

1. Field of the Invention

The present disclosure relates to an information processing apparatus, an information processing method, and a program.

2. Description of the Related Art

In related art, a technology for generating a calculation expression for function approximation through machine learning using learning data is disclosed (see JP-H07-065168A). In this technology, the calculation expression for function approximation is changed through relearning using added learning data.

A technology for identifying a behavior of a user by inputting sensor data acquired from the behavior of the user to a discriminator acquired in advance through the machine learning using the learning data is disclosed (see JP2013-041323A).

In this technology, in a case where the user inputs the fact that an identification result is incorrect, a behavior as a correction candidate is presented to the user, and the user selects the behavior. In this technology, the discriminator relearns by using sensor data and the behavior selected by the user.

SUMMARY OF THE INVENTION

However, in the technologies described in JP1995-065168A (JP-H07-065168A) and JP2013-041323A, since it is not considered how much correction has been performed by the user for output data output from a learned model, appropriate relearning data is not able to be accumulated. The relearning data mentioned herein indicates data used in the relearning of the learned model acquired through the machine learning.

The present disclosure has been made in view of the aforementioned circumstances, and an object of the present disclosure is to provide an information processing apparatus, an information processing method, and a program capable of accumulating appropriate relearning data.

In order to achieve the object, an information processing apparatus of the present disclosure comprises an input unit that inputs input data to a learned model acquired in advance through machine learning using learning data, an acquisition unit that acquires output data output from the learned model through the input using the input unit, a reception unit that receives correction performed by a user for the output data acquired by the acquisition unit, and a storage controller that performs control for storing, as relearning data of the learned model, the input data and the output data that reflects the correction received by the reception unit in a storage unit in a case where a value indicating a correction amount acquired by performing the correction for the output data is equal to or greater than a threshold value.

In the information processing apparatus of the present disclosure, the value indicating the correction amount may be a sum of an absolute value of a ratio of an added portion and an absolute value of a ratio of a deleted portion to and from the output data through the correction.

In the information processing apparatus of the present disclosure, the input data may be image data indicating a medical image, and the output data may be data indicating a region extracted from the image data.

In the information processing apparatus of the present disclosure, the value indicating the correction amount may be a ratio of a sum of an area of an added portion and an area of a deleted portion through the correction performed by the user received by the reception unit to an area of the region indicated by the output data.

In the information processing apparatus of the present disclosure, the value indicating the correction amount may be a ratio of a sum of a volume of an added portion and a volume of a deleted portion through the correction performed by the user received by the reception unit to a volume of the region indicated by the output data.

In the information processing apparatus of the present disclosure, the output data may be a sentence of a medical diagnostic report.

In the information processing apparatus of the present disclosure, the value indicating the correction amount may be the number of times the correction is performed by the user for the output data.

In the information processing apparatus of the present disclosure, the storage controller may perform the control in a case where the user is a user determined as a reliable user in advance.

In the information processing apparatus of the present disclosure, the threshold value may be a value which becomes smaller as a skill level of the user becomes higher.

In the information processing apparatus of the present disclosure, the threshold value may be a value determined depending on a treatment plan of a subject.

In the information processing apparatus of the present disclosure, the threshold value may be 10%.

In the information processing apparatus of the present disclosure may further comprise a learning unit that causes the learned model to relearn by using the relearning data stored in the storage unit by the storage controller.

In order to achieve the object, an information processing method by a computer of the present disclosure comprises inputting input data to a learned model acquired in advance through machine learning using learning data, acquiring output data output from the learned model through the input, receiving correction performed by a user for the acquired output data, and performing control for storing, as relearning data of the learned model, the input data and the output data that reflects the received correction in a storage unit in a case where a value indicating a correction amount acquired by performing the correction for the output data is equal to or greater than a threshold value.

In order to achieve the object, a program of the present disclosure causes a computer to execute inputting input data to a learned model acquired in advance through machine learning using learning data, acquiring output data output from the learned model through the input, receiving correction performed by a user for the acquired output data, and performing control for storing, as relearning data of the learned model, the input data and the output data that reflects the received correction in a storage unit in a case where a value indicating a correction amount acquired by performing the correction for the output data is equal to or greater than a threshold value.

An information processing apparatus of the present disclosure comprises a memory that stores a command to be executed by a computer, and a processor that is configured to execute the stored command. The processor inputs input data to a learned model acquired in advance through machine learning using learning data, acquires output data output from the learned model through the input, receives correction performed by a user for the acquired output data, and performs control for storing, as relearning data of the learned model, the input data and the output data that reflects the received correction in a storage unit in a case where a value indicating a correction amount acquired by performing the correction for the output data is equal to or greater than a threshold value.

According to the present disclosure, it is possible to accumulate appropriate relearning data.

DESCRIPTION OF THE PREFERRED EMBODIMENTS

Hereinafter, form examples for implementing a technology of the present disclosure will be described in detail.

First Embodiment

Figure 1:
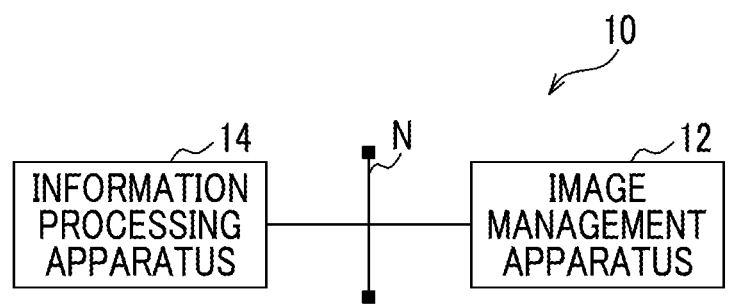
FIG. 1 is a block diagram showing an example of a configuration of a diagnostic support system according to embodiments.

Initially, a configuration of a diagnostic support system 10 according to the present embodiment will be described with reference to FIG. 1. As shown in FIG. 1, the diagnostic support system 10 includes an image management apparatus 12 and an information processing apparatus 14. The image management apparatus 12 and the information processing apparatus 14 are connected to a network N, and can communicate via the network N. The image management apparatus 12 stores image data (hereinafter, referred to as "medical image data") indicating a medical image acquired through imaging using an imaging device that images medical images of computed tomography (CT) and magnetic resonance imaging (MRI). Examples of the image management apparatus 12 include a picture archiving and communication system (PACS). The information processing apparatus 14 supports diagnosis by using the medical image data stored in the image management apparatus 12. Examples of the information processing apparatus 14 include a personal computer and a server computer.

Figure 2:
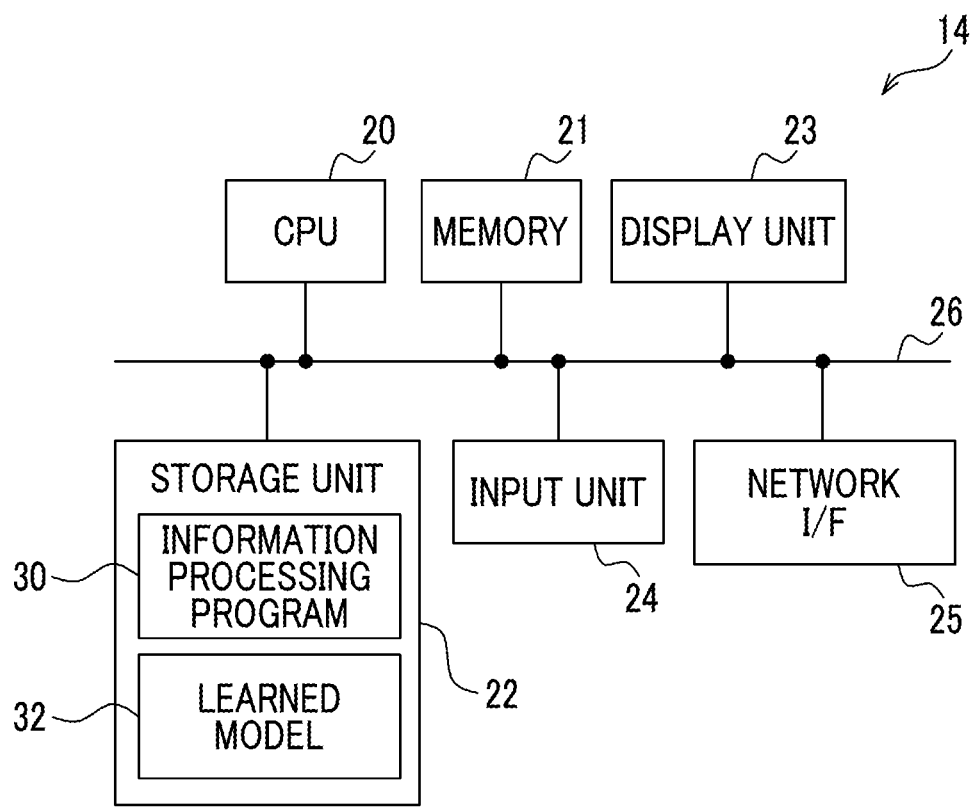
FIG. 2 is a block diagram showing an example of a hardware configuration of an information processing apparatus according to the embodiments.

Next, a hardware configuration of the information processing apparatus 14 according to the present embodiment will be described with reference to FIG. 2. As shown in FIG. 2, the information processing apparatus 14 includes a central processing unit (CPU) 20, a memory 21 as a temporary storage region, and a nonvolatile storage unit 22. The information processing apparatus 14 includes a display unit 23 such as a liquid crystal display, an input unit 24 such as a keyboard and a mouse, and a network interface (IF) 25 connected to the network N. The CPU 20, the memory 21, the storage unit 22, the display unit 23, the input unit 24, and the network I/F 25 are connected to a bus 26.

The storage unit 22 is implemented by a hard disk drive (HDD), a solid-state drive (SSD), and a flash memory. An information processing program 30 is stored in the storage unit 22 as a storage medium. The CPU 20 reads out the information processing program 30 from the storage unit 22, develops the readout information processing program into the memory 21, and executes the developed information processing program 30.

Figure 3:
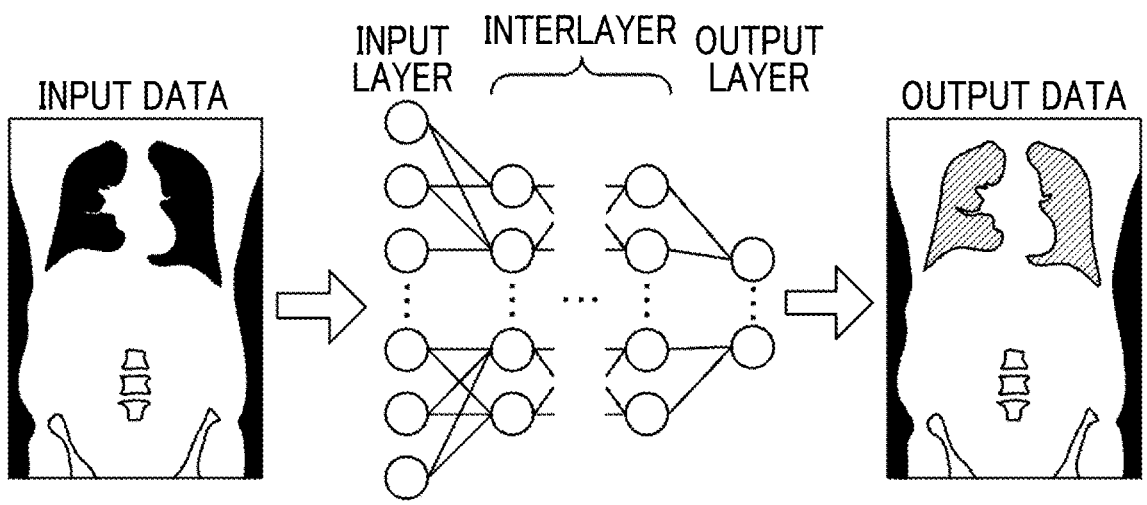
FIG. 3 is a diagram showing an example of a learned model according to a first embodiment.

A learned model 32 is stored in the storage unit 22. The learned model 32 will be described with reference to FIG. 3. As shown in FIG. 3, a form example in which a neural network including an input layer, a plurality of interlayers, and an output layer is applied as an example of the learned model 32 will be described in the present embodiment.

The medical image data acquired through the imaging using CT is input, as an example of the input data, to the learned model 32. Data indicating a region extracted from the medical image data is output, as an example of output data, from the learned model 32. In the present embodiment, the learned model 32 extracts lung regions on a medical image indicated by the input medical image data, and outputs image data indicating an image acquired by filling the extracted lung regions with a predetermined color (for example, red). In FIG. 3, the extracted lung regions are represented by diagonal regions.

Although a case where the learned model 32 extracts the lung regions on both left and right sides has been described in the present embodiment, the present disclosure is not limited thereto. The learned model 32 may extract the lung region on any one of the left and right sides, may extract regions other than the lung regions, or may extract multiple kinds of regions. Examples of the regions extracted by the learned model 32 include an organ region, a bone region, a blood vessel region, and a subcutaneous fat region.

The learned model 32 is a model acquired in advance by machine learning using, as learning data (referred to as training data), multiple sets of medical image data and data indicating the lung regions of the medical image data. Examples of a method used in the machine learning in this case include an error back-propagation method.

Figure 4:
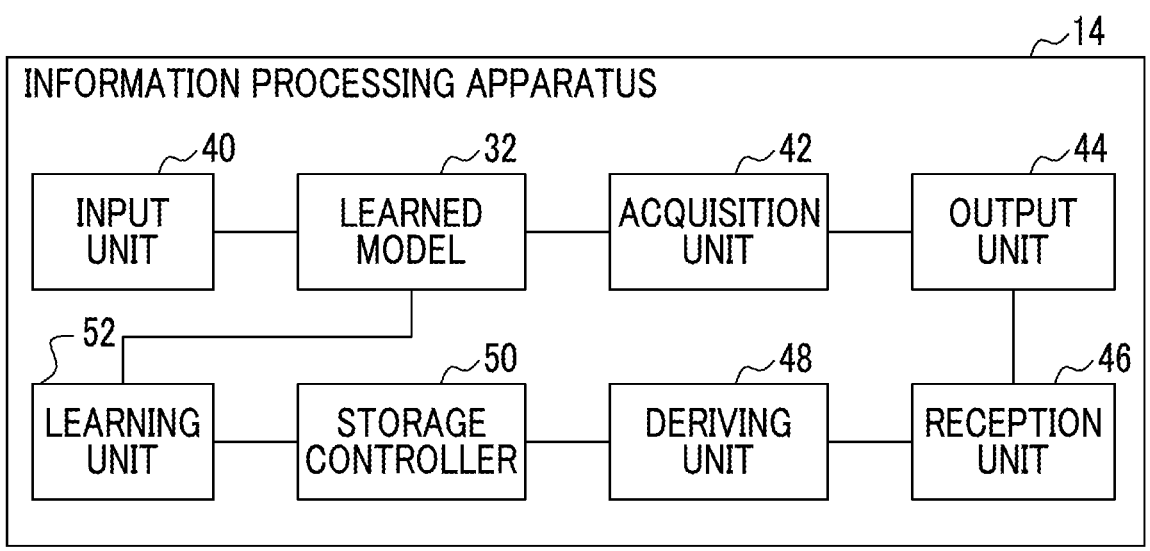
FIG. 4 is a block diagram showing an example of a functional configuration of the information processing apparatus according to the first embodiment.

Next, a functional configuration of the information processing apparatus 14 according to the present embodiment will be described with reference to FIG. 4. As shown in FIG. 4, the information processing apparatus 14 includes an input unit 40, an acquisition unit 42, an output unit 44, a reception unit 46, a deriving unit 48, a storage controller 50, and a learning unit 52. The CPU 20 executes the information processing program 30, and thus, the information processing program functions as the input unit 40, the acquisition unit 42, the output unit 44, the reception unit 46, the deriving unit 48, the storage controller 50, and the learning unit 52.

The input unit 40 acquires the medical image data from the image management apparatus 12, and inputs the acquired medical image data to the learned model 32. The acquisition unit 42 acquires the output data output from the learned model 32 so as to correspond to the input from the input unit 40.

The output unit 44 outputs the output data acquired by the acquisition unit 42 to the display unit 23. Through this output, the image acquired by filling the lung regions with the predetermined color is displayed on the display unit 23. A user confirms the image displayed on the display unit 23, and corrects the lung regions on the image to correct regions through the input unit 24 in a case where correction is necessary.

Figure 5:
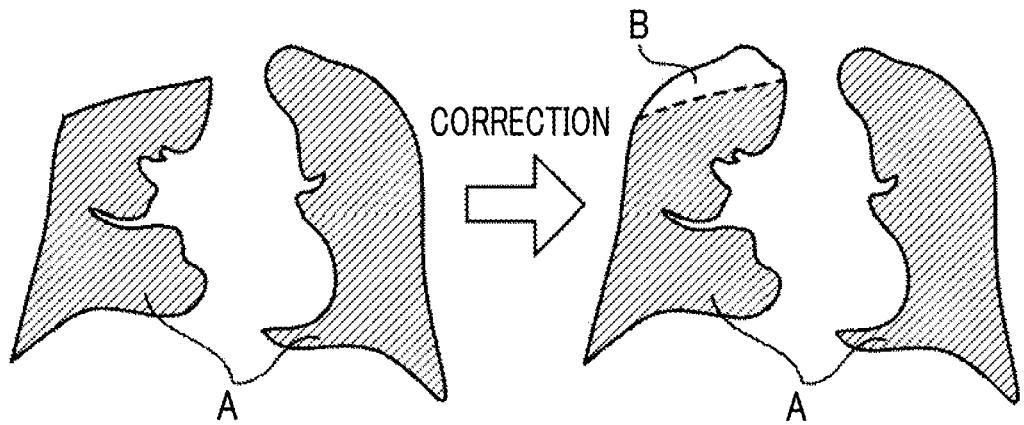
FIG. 5 is a diagram showing an example in which a region is added by a user according to the first embodiment.

For example, as shown in FIG. 5, in a case where the extracted lung regions are narrower than the actual regions, the user performs correction for adding a region. In the example of FIG. 5, diagonal regions A indicate the lung regions extracted by the learned model 32, and a white region B indicates a region added by the user through the correction.

Figure 6:
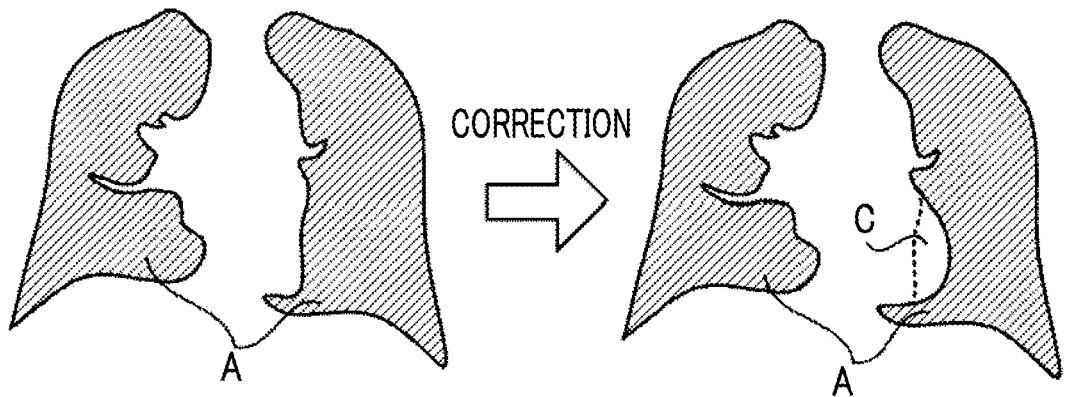
FIG. 6 is a diagram showing an example in which a region is deleted by the user according to the first embodiment.

For example, as shown in FIG. 6, in a case where the extracted lung regions are wider than the actual regions, the user performs correction for deleting a region. In the example of FIG. 6, the diagonal regions A indicate the lung regions extracted by the learned model 32, and a white region C indicates a region deleted by the user through the correction.

Figure 7:
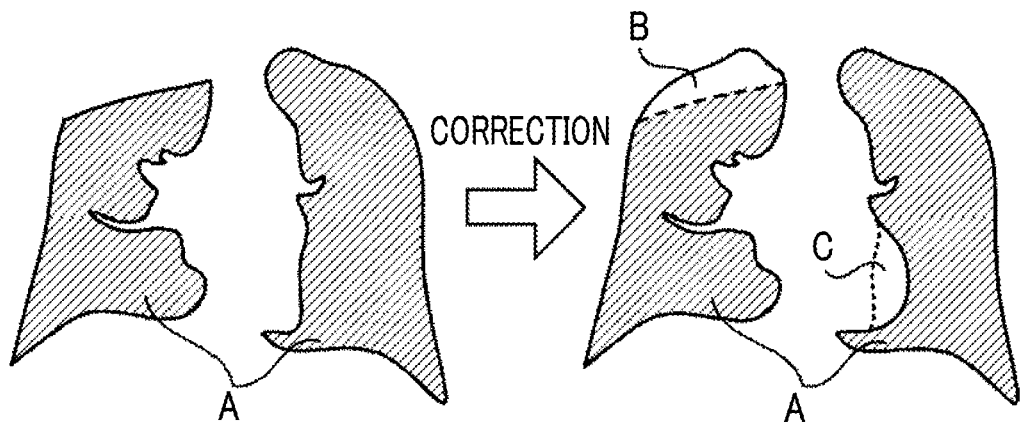
FIG. 7 is a diagram showing an example in which the region is added and deleted by the user according to the first embodiment.

For example, as shown in FIG. 7, the user may perform both the correction for adding the region B and deleting the region C to and from the extracted lung regions.

The reception unit 46 receives the correction performed by the user for the output data output by the output unit 44. Specifically, the reception unit 46 receives the output data that reflects the correction of the region performed by the user as stated above.

The deriving unit 48 derives a value indicating a correction amount through the correction received by the reception unit 46 for the output data output by the output unit 44. In the present embodiment, the deriving unit 48 derives the sum of an absolute value of a ratio of an added portion and an absolute value of a ratio of a deleted portion to and from the output data through the correction. For example, as in the example shown in FIG. 5, in a case where there is the added region and there is no deleted region, since the absolute value of the ratio of the deleted portion to the output data is zero, the sum is the absolute value of the ratio of the added portion. For example, as in the example shown in FIG. 6, in a case where there is the deleted region and there is not added region, since the absolute value of the ratio of the added portion to the output data is zero, the sum is the absolute value of the ratio of the deleted portion.

Specifically, the deriving unit 48 derives, as the value indicating the correction amount, a ratio of the sum of an area of the added portion (the region B in the examples of FIGS. 5 and 7) and an area of the deleted portion (the region C in the examples of FIGS. 6 and 7) through the correction received by the reception unit 46 to an area of the lung regions (regions A in the examples of FIGS. 5 to 7) extracted by the learned model 32. For example, this ratio can be obtained by dividing the sum of the area of the region B and the area of the region C by the area of the region A. For example, the area of each region may be the number of pixels of the image, or may be an area acquired by converting the number of pixels into an actual size.

The deriving unit 48 may derive the value indicating the correction amount by using a volume instead of the area. In this case, a form in which pixels of a portion of a plurality of medical images indicated by a plurality of medical image data items acquired by performing CT imaging once which is corrected by the user are used as voxels and the number of voxels is used as a volume is illustrated.

In case where the value indicating the correction amount derived by the deriving unit 48 is equal to or greater than a threshold value, the storage controller 50 performs control for storing, as relearning data of the learned model 32, the input data input to the learned model 32 by the input unit 40 and the output data that reflects the correction received by the reception unit 46 in the storage unit 22.

In the present embodiment, a value determined depending on a treatment plan for a disease of a subject is used as the threshold value. As a specific example, the following prescription conditions (1) and (2) are set for medicine of polycystic kidney disease depending on the volume of the kidney.

(1) An increase rate in volume of the kidney is 5%/year or more.

(2) A total kidney volume is 750 ml or more.

As stated above, in a case where an error of 5% or more occurs at the time of measuring the volume of the kidney, the treatment plan of the disease of the subject is influenced. In this example, 5% is used as the threshold value, and the storage controller 50 performs control for storing the relearning data in the storage unit 22 in a case where the value indicating the correction amount derived by the deriving unit 48 is equal to or greater than 5%.

A value corresponding to extraction accuracy of a required region may be used as the threshold value. For example, in a case where DICE accuracy indicating the region extraction in machine learning exceeds 90%, it is difficult to recognize a difference in accuracy at a glance. Thus, the influence may be less for correction of less than 10%, and 10% may be used as the threshold value. In this case, the storage controller 50 performs control for storing the relearning data in the storage unit 22 in a case where the value indicating the correction amount derived by the deriving unit 48 is equal to or greater than 10%. A value set by the user may be used as the threshold value.

The learning unit 52 causes the learned model 32 to relearn by using the relearning data stored in the storage unit 22 under the control of the storage controller 50. Examples of a method used in the relearning include an error back-propagation method.

Next, the actions of the information processing apparatus 14 according to the present embodiment will be described with reference to FIGS. 8 and 9. The CPU 20 executes the information processing program 30, and thus, a storage control process shown in FIG. 8 and a relearning process shown in FIG. 9 are performed. For example, the storage control process shown in FIG. 8 is performed in a case where an execution command of the storage control process is input by the user through the input unit 24.

Figure 8:
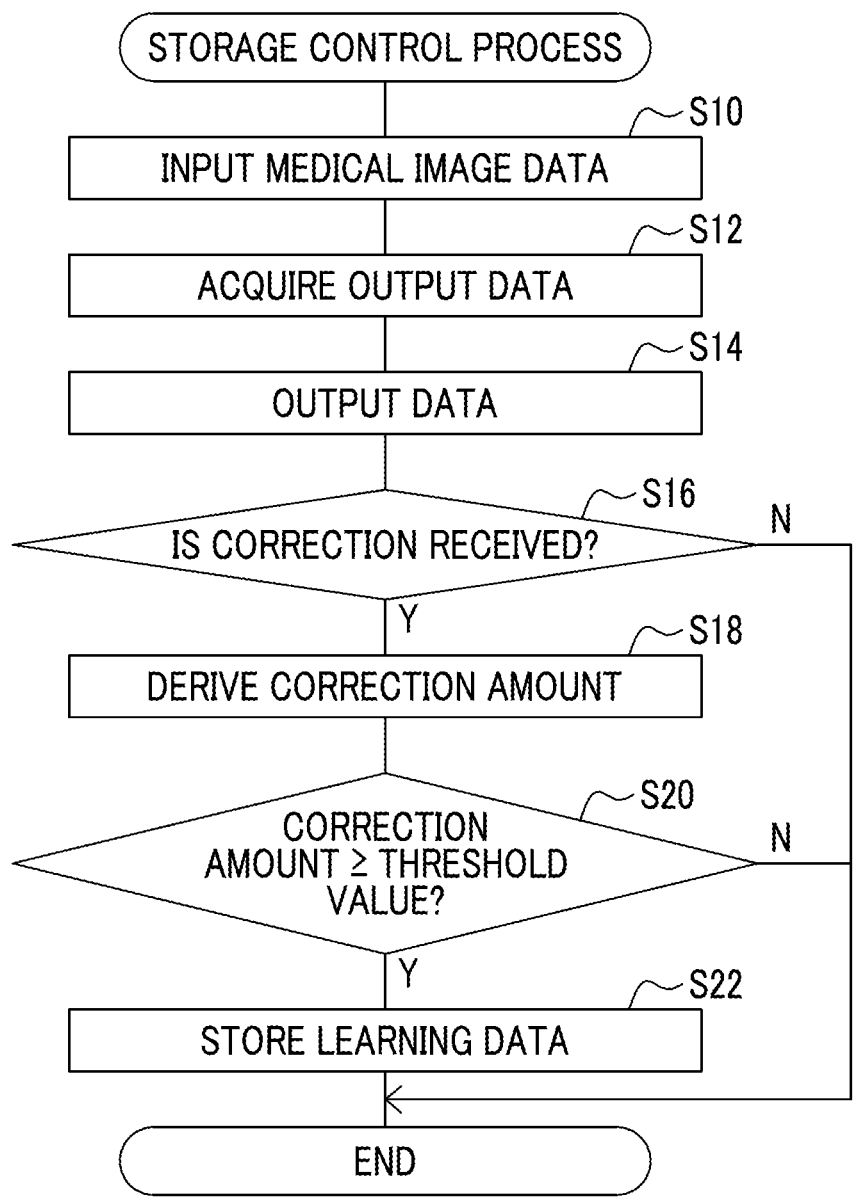
FIG. 8 is a flowchart showing an example of a storage control process according to the first embodiment.
Figure 9:
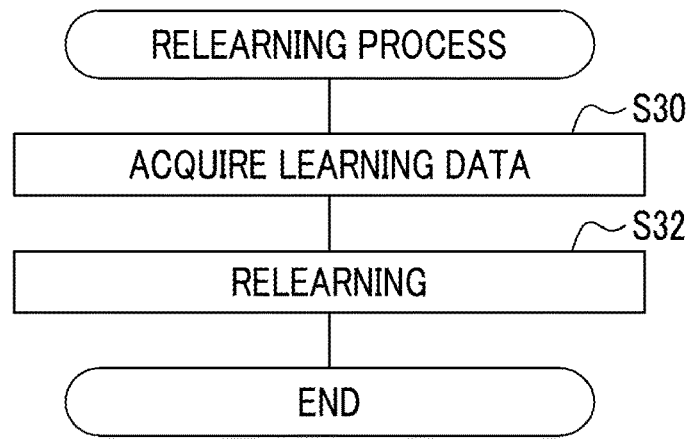
FIG. 9 is a flowchart showing an example of a relearning process according to the first embodiment.

In step S10 of FIG. 8, the input unit 40 acquires the medical image data from the image management apparatus 12, and inputs the acquired medical image data to the learned model 32. In step S12, the acquisition unit 42 acquires the output data output from the learned model 32 so as to correspond to the input through the process of step S10.

In step S14, the output unit 44 outputs the output data acquired through the process of step S12 to the display unit 23 as stated above. In step S16, the reception unit 46 determines whether or not the correction performed by the user for the output data output through the process of step S14 is received as stated above. In a case where this determination is positive determination, the process proceeds to step S18.

In step S18, the deriving unit 48 derives the value indicating the correction amount through the correction received through the process of step S16 for the output data output through the process of step S14 as stated above. In step S20, the storage controller 50 determines whether or not the value indicating the correction amount derived through the process of step S18 is equal to or greater than the threshold value as stated above. In a case where this determination is positive determination, the process proceeds to step S22.

In step S22, the storage controller 50 performs control for storing, as the relearning data of the learned model 32, the input data input to the learned model 32 through the process of step S10 and the output data that reflects the correction received through the process of step S16 in the storage unit 22. In a case where the process of step S22 is ended, the storage control process is ended.

Meanwhile, in a case where the determination of step S16 is negative determination, the processes of steps S18, S20, and S22 are not performed, and the storage control process is ended. In a case where the determination of step S20 is negative determination, the process of step S22 is not performed, and the storage control process is ended.

Through the storage control process shown in FIG. 8, in a case where a predetermined number (for example, 100) of relearning data items are stored in the storage unit 22, the relearning process shown in FIG. 9 is performed. The relearning process shown in FIG. 9 may be performed whenever the relearning data is stored in the storage unit 22 through the process of step S22 of FIG. 8, or may be performed in a case where the execution command is input by the user.

In step S30 of FIG. 9, the learning unit 52 acquires the relearning data stored in the storage unit 22 through the storage control process shown in FIG. 8. In step S32, the learning unit 52 causes the learned model 32 to relearn by using the relearning data acquired through the process of step S30. In a case where the process of step S32 is ended, the relearning process is ended.

As described above, according to the present embodiment, in a case where the value indicating the correction amount through the correction performed by the user for the output data is equal to or greater than the threshold value, the control for storing, as the relearning data of the learned model 32, the input data and the output data that reflects the correction in the storage unit 22 is performed. Accordingly, it is possible to accumulate appropriate relearning data.

Second Embodiment

The form example in which the medical image data is a processing target has been described in the first embodiment. A form example in which the medical diagnostic report is a processing target will be described in the present embodiment. A configuration (see FIG. 1) of the diagnostic support system 10 and a hardware configuration (see FIG. 2) of the information processing apparatus 14 according to the present embodiment are the same as those in the first embodiment, and thus, the description thereof will be omitted.

Figure 10:
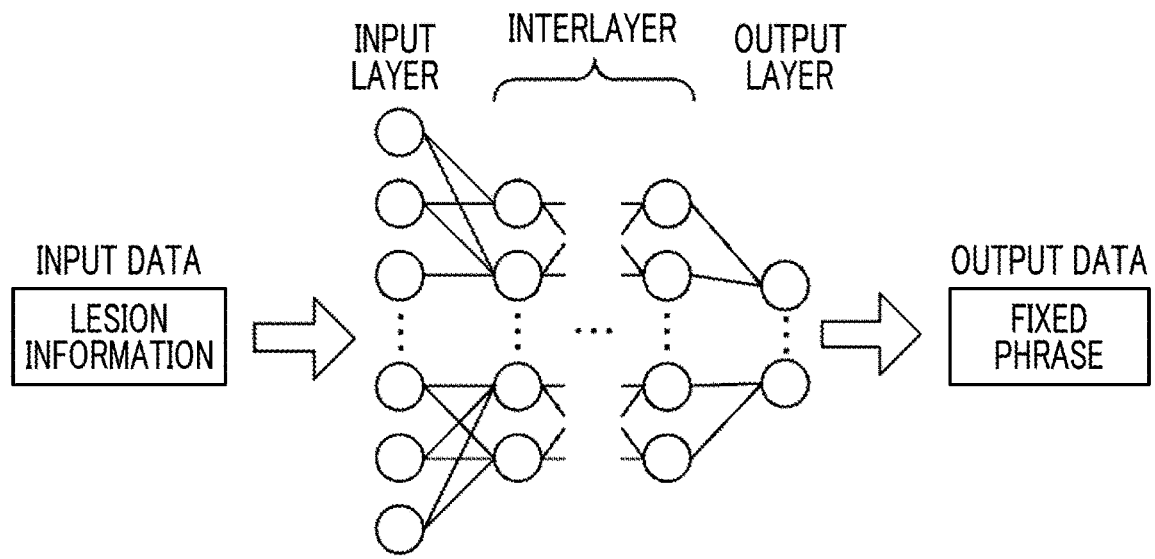
FIG. 10 is a diagram showing an example of a learned model according to a second embodiment.

The learned model 32 stored in the storage unit 22 according to the present embodiment will be described with reference to FIG. 10. As shown in FIG. 10, a form example in which a neural network including an input layer, a plurality of interlayers, and an output layer is applied as an example of the learned model 32 will be described in the present embodiment.

Lesion information acquired as a result of a diagnostic support process is input as an example of the input data to the learned model 32. Examples of the diagnostic support process include lung computer-aided diagnosis (CAD), and examples of the lesion information include qualitative information such as a size of a lesion and a signal value of the CT image. A fixed phrase used as a sentence of a medical diagnostic report is output as the example of the output data from the learned model 32.

The learned model 32 is a model acquired in advance through the machine learning using multiple sets of lesion information items and the sentence of the medical diagnostic report as the learning data. Examples of a method used in the machine learning in this case include an error back-propagation method.

Figure 11:
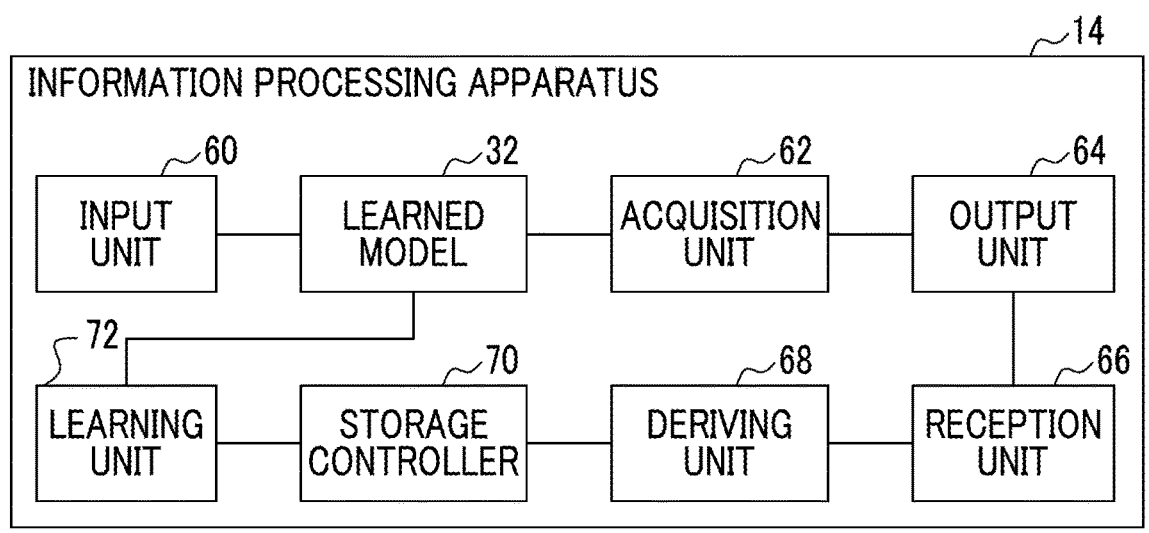
FIG. 11 is a block diagram showing an example of a functional configuration of an information processing apparatus according to the second embodiment.

Next, a functional configuration of the information processing apparatus 14 according to the present embodiment will be described with reference to FIG. 11. As shown in FIG. 11, the information processing apparatus 14 includes an input unit 60, an acquisition unit 62, an output unit 64, a reception unit 66, a deriving unit 68, a storage controller 70, and a learning unit 72. The CPU 20 executes the information processing program 30, and the information processing program functions as the input unit 60, the acquisition unit 62, the output unit 64, the reception unit 66, the deriving unit 68, the storage controller 70, and the learning unit 72.

The input unit 60 acquires the lesion information acquired as the result of the diagnostic support process from the image management apparatus 12, and inputs the acquired lesion information to the learned model 32. The acquisition unit 62 acquires the output data output from the learned model 32 so as to correspond to the input through the input unit 60.

The output unit 64 outputs the output data acquired by the acquisition unit 62 to the display unit 23. Through this output, a fixed phrase used as the sentence of the medical diagnostic report is displayed on the display unit 23. The user confirms a word (for example, the size of the lesion) and a sentence style indicating features of the fixed phrase displayed on the display unit 23, and corrects the fixed phrase to a correct sentence through the input unit 24 in a case where correction is necessary.

The reception unit 66 receives correction performed by the user for the output data output by the output unit 64. Specifically, the reception unit 66 receives the sentence that reflects the correction performed by the user as stated above.

The deriving unit 68 derives the value indicating the correction amount through the correction received by the reception unit 66 for the output data output by the output unit 64. In the present embodiment, the deriving unit 68 derives the sum of the absolute value of the ratio of the added portion and the absolute value of the ratio of the deleted portion to and from the output data through the correction. For example, in a case where there is an added character and there is no deleted character, since the absolute value of the ratio of the deleted portion to the output data is zero, the sum is the absolute value of the ratio of the added portion. For example, in a case where there is the deleted character and there is no added character, since the absolute value of the ratio of the added portion to the output data is zero, the sum is the absolute value of the ratio of the deleted portion.

Specifically, the deriving unit 68 derives, as the value indicating the correction amount, a ratio of the sum of the number of added characters and the number of deleted characters through the correction received by the reception unit 66 to the number of characters of the fixed phrase output from the learned model 32. The deriving unit 68 may derive, as the value indicating the correction amount, a ratio of the sum of the number of added words and the number of deleted words through the correction received by the reception unit 66 to the number of words of the fixed phrase output from the learned model 32.

In a case where the value indicating the correction amount derived by the deriving unit 68 is equal to or greater than the threshold value, the storage controller 70 performs control for storing, as the relearning data of the learned model 32, the input data input to the learned model 32 by the input unit 60 and the output data that reflects the correction received by the reception unit 66 in the storage unit 22.

The learning unit 72 causes the learned model 32 to relearn by using the relearning data stored in the storage unit 22 under the control of the storage controller 70. Examples of a method used in the relearning include an error backpropagation method.

Next, the actions of the information processing apparatus 14 according to the present embodiment will be described with reference to FIGS. 12 and 13. The CPU 20 executes the information processing program 30, and thus, a storage control process shown in FIG. 12 and a relearning process shown in FIG. 13 are performed. For example, a diagnostic support process shown in FIG. 12 is performed in a case where an execution command of the storage control process is input by the user through the input unit 24.

Figure 12:
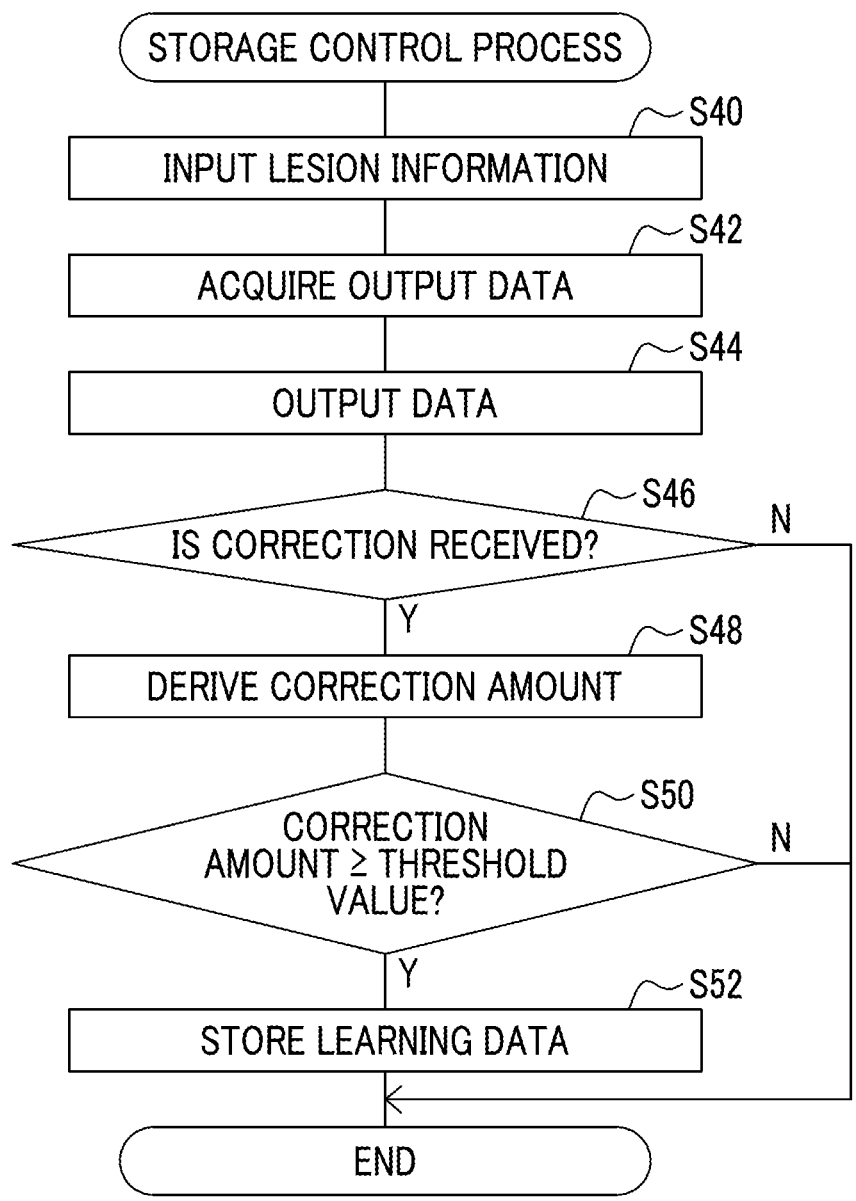
FIG. 12 is a flowchart showing an example of a storage control process according to the second embodiment.
Figure 13:
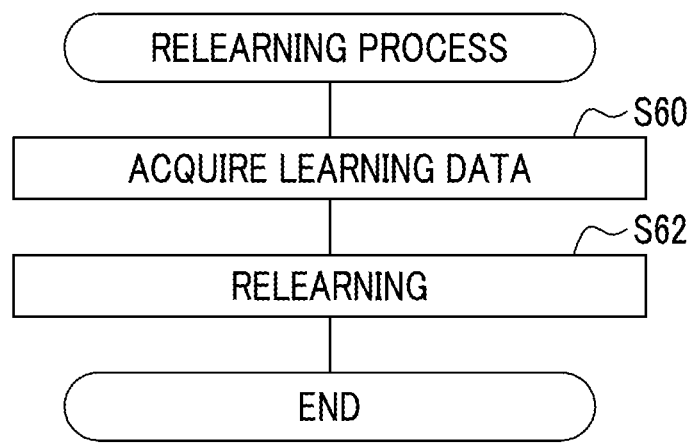
FIG. 13 is a flowchart showing an example of a relearning process according to the second embodiment.

In step S40 of FIG. 12, the input unit 40 acquires the lesion information acquired as the result of the diagnostic support process from the image management apparatus 12, and inputs the acquired lesion information to the learned model 32. In step S42, the acquisition unit 62 acquires the output data output from the learned model 32 so as to correspond to the input through the process of step S40.

In step S44, the output unit 64 outputs the output data acquired through the process of step S42 to the display unit 23 as stated above. In step S46, the reception unit 66 determines whether or not the correction performed by the user for the output data output through the process of step S44 is received as stated above. In a case where this determination is positive determination, the process proceeds to step S48.

In step S48, the deriving unit 68 derives the value indicating the correction amount through the correction received through the process of step S46 for the output data output through the process of step S44. In step S50, the storage controller 70 determines whether or not the value indicating the correction amount derived through the process of step S48 is equal to or greater than the threshold value as stated above. In a case where this determination is positive determination, the process proceeds to step S52.

In step S52, the storage controller 70 performs control for storing, as the relearning data of the learned model 32, the input data input to the learned model 32 through the process of step S40 and the output data that reflects the correction received through the process of step S46 in the storage unit 22. In a case where the process of step S52 is ended, the storage control process is ended.

Meanwhile, in a case where the determination of step S46 is negative determination, the processes of steps S48, S50, and S52 are not performed, and the storage control process is ended. In a case where the determination of step S50 is negative determination, the process of step S52 is not performed, and the storage control process is ended.

Through the storage control process shown in FIG. 12, in a case where a predetermined number (for example, 100) of relearning data items are stored in the storage unit 22, the relearning process shown in FIG. 13 is performed. The relearning process shown in FIG. 13 may be performed whenever the relearning data is stored in the storage unit 22 through the process of step S52 of FIG. 12, and may be performed when the execution command is input by the user.

In step S60 of FIG. 13, the learning unit 72 acquires the relearning data stored in the storage unit 22 through the storage control process shown in FIG. 12. In step S62, the learning unit 72 causes the learned model 32 to relearn by using the relearning data acquired through the process of step S60 as stated above. In a case where the process of step S62 is ended, the relearning process is ended.

As described above, according to the present embodiment, it is possible to acquire the same effects as those in the first embodiment.

Although a case where the disclosed technology is applied to the medical field has been described in the embodiments, the present disclosure is not limited thereto. A form in which the disclosed technology is applied to fields other than the medical field may be used.

The value indicating the correction amount in the embodiment may be the number of times the correction is performed for the output data output from the output unit 44 or 64 by the user. In this case, for example, in a case where N (N is an integer of 2 or more) output data items are continuously corrected, a form in which the relearning data is stored in the storage unit 22 is illustrated. In this case, in a case where a ratio of the number of times the correction is performed to a predetermined number (for example, 10) of output data items is equal to or greater than a threshold value (for example, 80%), a form in which the relearning data is stored in the storage unit 22 is illustrated.

In the embodiment, in a case where a user who corrects the output data is a user determined as a reliable user, control for storing the relearning data in the storage unit 22 may be performed. In this case, a form in which a doctor, a radiologist, and an engineer among a doctor, a radiologist, an engineer, a resident, and a guest are registered as reliable users is illustrated.

A value which becomes smaller as a skill level of the user becomes higher may be used as the threshold value compared with the value indicating the correction amount in the embodiment. In this case, for example, a threshold value in a case where the user is a medical specialist as an expert is a value smaller than a threshold value in a case where the user is the resident as an inexperienced doctor. As the skill level of the user becomes higher, the accuracy of the correction is high in many cases. Accordingly, it is possible to accumulate appropriate relearning data by using the value which becomes smaller as the skill level of the user becomes higher as the threshold value.

In the embodiment, for example, various processors to be described below can be used as hardware structures of the processing units that perform various processes such as the input unit, the acquisition unit, the output unit, the reception unit, the deriving unit, the storage controller, and the learning unit. As stated above, examples of various processors include a programmable logic device (PLD) such as a field-programmable gate array (FPGA) which is a processor of which a circuit configuration can be changed after being manufactured, a dedicated electric circuit such as an application specific integrated circuit (ASIC) which is a processor having a circuit configuration designed as a dedicated circuit in order to perform a specific process in addition to the CPU which is a general-purpose processor functioning as various processing units by executing software (program).

One processing unit may be constituted by one of these various processors, or may be constituted by a combination (for example, a combination of a plurality of FPGAs or a combination of the CPU and the FPGA) of the same kind or different kinds of two or more processors. Alternatively, the plurality of processing units may be constituted by one processor.

Firstly, as the example in which the plurality of processing units is constituted by one processor, there is a form in which one processor is constituted by a combination of one or more CPUs and software and this processor functions as the plurality of processing units as represented by computers such as a client and a server. Secondly, there is a form in which a processor that implements the entire system function including the plurality of processing units by one integrated circuit (IC) chip as represented by a system on chip (SoC) is used. As stated above, various processing units are constituted as hardware structure by using one or more of various processors.

More specifically, an electric circuitry acquired by combining circuit elements such as semiconductor elements can be used as the hardware structure of these various processors.

Although the aspect in which the information processing program 30 is stored (installed) in advance in the storage unit 22 has been described in the embodiment, the present disclosure is not limited thereto. The information processing program 30 may be provided while being recorded in a recording medium such as a compact disc read only memory (CD-ROM), a digital versatile disc read only memory (DVD-ROM), and a universal serial bus (USB) memory. The information processing program 30 may be downloaded from an external device via a network.

Explanation of References
- 10: diagnostic support system
- 12: image management apparatus
- 14: information processing apparatus
- 20: CPU
- 21: memory
- 22: storage unit
- 23: display unit
- 24: input unit
- 25: network I/F
- 26: bus
- 30: information processing program
- 32: learned model
- 40, 60: input unit
- 42, 62: acquisition unit
- 44, 64: output unit
- 46, 66: reception unit
- 48, 68: deriving unit
- 50, 70: storage controller
- 52, 72: learning unit
- N: network

What is claimed is:

1. An information processing apparatus comprising:
a memory; and
a processor, coupled to the memory and configured to:
input data into a learned model, wherein the learned model is a machine learning model trained in advance on learning data and wherein the data is medical image data;
acquire output data from the learned model through inputting the data,
wherein the output data includes a portion extracted from the input data,
wherein the portion extracted from the input data is a region extracted from the medical image data;
receive correction performed by a user for the acquired output data to generate a corrected output data including an added portion that is added to the extracted portion of the output data and a deleted portion that is deleted from the extracted portion of the output data;
store, as relearning data of the learned model, the input data and the corrected output data in the memory in a case where a value indicating a correction amount acquired by performing the correction for the output data is equal to or greater than a threshold value,
wherein the value indicating the correction amount is a sum of an absolute value of a ratio of the added portion to the extracted portion and an absolute value of a ratio of the deleted portion to the extracted portion; and
retrain the learned model by using the stored relearning data.

2. The information processing apparatus according to claim 1,
wherein the input data is image data indicating a medical image, and
the portion extracted from the input data is a region extracted from the image data.

3. The information processing apparatus according to claim 2,
wherein the value indicating the correction amount is a ratio of a sum of an area of the added portion and an area of the deleted portion through the received correction performed by the user to an area of the region indicated by the output data.

4. The information processing apparatus according to claim 2,
wherein the value indicating the correction amount is a ratio of a sum of a volume of the added portion and a volume of the deleted portion through the correction performed by the user to a volume of the region indicated by the output data.

5. The information processing apparatus according to claim 1,
wherein the output data is a sentence of a medical diagnostic report.

6. The information processing apparatus according to claim 1,
wherein the value indicating the correction amount is the number of times the correction is performed by the user for the output data.

7. The information processing apparatus according to claim 1,
wherein the threshold value is selected based on a skill level of the user prior to the generation of relearning data.

8. The information processing apparatus according to claim 1,
wherein the threshold value is a value determined depending on a treatment plan of a subject.

9. The information processing apparatus according to claim 1,
wherein the threshold value is 10%.

10. An information processing method, executed by a computer, comprising:
inputting data into a learned model, wherein the learned model is a machine learning model trained in advance on learning data and wherein the data is medical image data;
acquiring output data from the learned model through inputting the data, wherein the output data includes a portion extracted from the input data, wherein the portion extracted from the input data is a region extracted from the medical image data;
receiving correction performed by a user for the acquired output data to generate a corrected output data including an added portion that is added to the extracted portion of the output data and a deleted portion that is deleted from the extracted portion of the output data;
storing, as relearning data of the learned model, the input data and the corrected output data in the memory in a case where a value indicating a correction amount acquired by performing the correction for the output data is equal to or greater than a threshold value,
wherein the value indicating the correction amount is a sum of an absolute value of a ratio of the added portion to the extracted portion and an absolute value of a ratio of the deleted portion to the extracted portion; and
retraining the learned model by using the stored relearning data.

11. An non-transitory computer readable medium storing a program causing a computer to execute a process comprising:
inputting data into a learned model, wherein the learned model is a machine learning model trained in advance on learning data and wherein the data is medical image data;
acquiring output data from the learned model through inputting the data, wherein the output data includes a portion extracted from the input data, wherein the portion extracted from the input data is a region extracted from the medical image data;
receiving correction performed by a user for the acquired output data to generate a corrected output data including an added portion that is added to the extracted portion of the output data and a deleted portion that is deleted from the extracted portion of the output data;
storing, as relearning data of the learned model, the input data and the corrected output data in the memory in a case where a value indicating a correction amount acquired by performing the correction for the output data is equal to or greater than a threshold value,
wherein the value indicating the correction amount is a sum of an absolute value of a ratio of the added portion to the extracted portion and an absolute value of a ratio of the deleted portion to the extracted portion; and
retraining the learned model by using the stored relearning data.

\* \* \* \* \*